(12) United States Patent
Benjamin et al.

(10) Patent No.: US 7,446,111 B2
(45) Date of Patent: Nov. 4, 2008

(54) AMORPHOUS RAPAMYCIN 42-ESTER WITH 3-HYDROXY-2-(HYDROXYMETHYL)-2-METHYLPROPIONIC ACID AND ITS PHARMACEUTICAL COMPOSITIONS

(75) Inventors: Eric J. Benjamin, Jamestown, NC (US); Muhammad Ashraf, Elmwood Park, NJ (US); Ashwinkumar Jain, Nanuet, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/891,500

(22) Filed: Aug. 10, 2007

(65) Prior Publication Data

US 2008/0070950 A1    Mar. 20, 2008

Related U.S. Application Data

(62) Division of application No. 10/930,487, filed on Aug. 31, 2004, now Pat. No. 7,271,177.

(60) Provisional application No. 60/499,789, filed on Sep. 3, 2003.

(51) Int. Cl.
*C07D 498/18* (2006.01)
*A61K 31/436* (2006.01)

(52) U.S. Cl. ........................... 514/291; 540/456

(58) Field of Classification Search ............... 540/456; 514/291
See application file for complete search history.

(56) References Cited

U.S. PATENT DOCUMENTS

| 5,362,718 | A | 11/1994 | Skotnicki et al. |
|---|---|---|---|
| 5,989,591 | A | 11/1999 | Nagi |
| 6,004,973 | A | 12/1999 | Guitard et al. |
| 6,197,781 | B1 | 3/2001 | Guitard et al. |
| 6,599,535 | B2 | 7/2003 | Guitard et al. |
| 7,271,177 | B2 | 9/2007 | Benjamin |
| 2004/0077677 | A1 | 4/2004 | Ashraf et al. |
| 2005/0152983 | A1 | 7/2005 | Ashraf et al. |

FOREIGN PATENT DOCUMENTS

| WO | WO 01/23395 A2 | 4/2001 |
|---|---|---|
| WO | WO 2004/026280 | 4/2004 |
| WO | WO 2005/070393 | 8/2005 |

OTHER PUBLICATIONS

Lee et al, Particle Size Reduction in "Water Insoluble Drug Formulations", (R. Liu, Ed.) Interpharm Press Co., Denver, CO 392-473, (2000).
Vippagunta et al, "Crystallline Solids", Adv. Drug Del. Rev., 48(1):3-26, (May 16, 2001).
Farmacia Hospitalaria, pp. 1590-1592, 2004.
Monographs on Chemical Derivatives, Stearic Acid, 2004.
Atkins, P., Physical Chemistry, 2nd Edition, 1996.

*Primary Examiner*—Bruck Kifle
(74) *Attorney, Agent, or Firm*—David Rubin; Howson & Howson LLP (57) ABSTRACT

The present invention provides an amorphous form of rapamycin 42-ester with 3-hydroxy-2-(hydroxymethyl)-2-methylpropionic acid. This invention also provides processes for preparing the amorphous form and pharmaceutical compositions including the amorphous form.

27 Claims, 7 Drawing Sheets

AMORPHOUS RAPAMYCIN 42-ESTER WITH 3-HYDROXY-2-(HYDROXYMETHYL)-2-METHYLPROPIONIC ACID AND ITS PHARMACEUTICAL COMPOSITIONS

CROSS-REFERENCE TO RELATED APPLICATIONS

This application is a divisional of U.S. patent application Ser. No. 10/930,487, filed Aug. 31, 2004, which claims the benefit of the priority of U.S. Provisional Patent Application No. 60/499,789, filed Sep. 3, 2003.

BACKGROUND OF THE INVENTION

This invention relates to a novel soluble form of rapamycin 42-ester with 3-hydroxy-2-(hydroxymethyl)-2-methylpropionic acid.

Crystalline rapamycin 42-ester with 3-hydroxy-2-(hydroxymethyl)-2-methylpropionic acid (CCI-779) has poor solubility, which leads to slow dissolution of the solid crystalline form, typically oral solid dosage forms including tablets, in physiologically acceptable solvents.

The dissolution and absorption of rapamycin 42-ester with 3-hydroxy-2-(hydroxymethyl)-2-methylpropionic acid has reportedly been improved by the formation of solid dispersions with carrier systems using co-precipitate technique, spray drying, use of nanoparticles, and wet granulation methods. However, while the art asserts that rapamycin can be in crystalline or amorphous form, amorphous rapamycin 42-ester with 3-hydroxy-2-(hydroxymethyl)-2-methylpropionic acid has never been previously prepared, isolated and/or characterized.

Since rapamycin 42-ester with 3-hydroxy-2-(hydroxymethyl)-2-methylpropionic acid is a therapeutically active compound, it is highly desirable to obtain amorphous rapamycin 42-ester with 3-hydroxy-2-(hydroxymethyl)-2-methylpropionic acid that has improved solubility, dissolution rate and bioavailability.

SUMMARY OF THE INVENTION

In one aspect, the present invention provides amorphous rapamycin 42-ester with 3-hydroxy-2-(hydroxymethyl)-2-methylpropionic acid. The amorphous form displays increased solubility over the crystalline form and is therefore useful for a variety of purposes, including for use in pharmaceutical compositions.

In another aspect, the present invention provides methods of preparing amorphous rapamycin 42-ester with 3-hydroxy-2-(hydroxymethyl)-2-methylpropionic acid.

In a further aspect, the present invention provides pharmaceutical compositions containing amorphous rapamycin 42-ester with 3-hydroxy-2-(hydroxymethyl)-2-methylpropionic acid.

In yet another aspect, the present invention provides kits containing amorphous rapamycin 42-ester with 3-hydroxy-2-(hydroxymethyl)-2-methylpropionic acid.

Other aspects and advantages of the present invention are described further in the following detailed description of the preferred embodiments thereof.

BRIEF DESCRIPTION OF THE FIGURES

FIGS. 1A-1D are X-ray diffraction (XRD) patterns of crystalline and amorphous ball mill ground rapamycin 42-ester with 3-hydroxy-2-(hydroxymethyl)-2-methylpropionic acid. FIG. 1A is the XRD pattern of crystalline rapamycin 42-ester with 3-hydroxy-2-(hydroxymethyl)-2-methylpropionic acid. FIGS. 1B-D are XRD patterns of ball mill ground rapamycin 42-ester with 3-hydroxy-2-(hydroxymethyl)-2-methylpropionic acid obtained after grinding for 20 minutes, 40 minutes, and 60 minutes.

FIGS. 3A-B are XRD patterns of amorphous rapamycin 42-ester with 3-hydroxy-2-(hydroxymethyl)-2-methylpropionic acid.

DETAILED DESCRIPTION OF THE INVENTION

The present invention provides amorphous rapamycin 42-ester with 3-hydroxy-2-(hydroxymethyl)-2-methylpropionic acid. Amorphous rapamycin 42-ester with 3-hydroxy-2-(hydroxymethyl)-2-methylpropionic acid was isolated and characterized by high performance liquid chromatography (HPLC), X-ray diffraction (XRD) and differential scanning calorimetry (DSC).

Amorphous rapamycin 42-ester with 3-hydroxy-2-(hydroxymethyl)-2-methylpropionic acid of the present invention overcomes the deficiencies of crystalline rapamycin 42-ester with 3-hydroxy-2-(hydroxymethyl)-2-methylpropionic acid. The amorphous form is at least 3 times more soluble than the crystalline form.

The following will provide further advantages of amorphous rapamycin 42-ester with 3-hydroxy-2-(hydroxymethyl)-2-methylpropionic acid and methods of obtaining and using the same.

I. Definitions

The term "dissolving solvent" is meant to describe a solvent that is capable of dissolving a solid. As used herein, the dissolving solvent includes any solvent that is capable of dissolving amorphous rapamycin 42-ester with 3-hydroxy-2-(hydroxymethyl)-2-methylpropionic acid, crystalline rapamycin 42-ester with 3-hydroxy-2-(hydroxymethyl)-2-methylpropionic acid, or a combination of amorphous and crystalline rapamycin 42-ester with 3-hydroxy-2-(hydroxymethyl)-2-methylpropionic acid.

The term "precipitation" is meant to describe a process by which a solid form of a compound is precipitated from a solution containing dissolved compound. As used herein, precipitation is meant to describe precipitating amorphous rapamycin 42-ester with 3-hydroxy-2-(hydroxymethyl)-2-methylpropionic acid from a solution of rapamycin 42-ester with 3-hydroxy-2-(hydroxymethyl)-2-methylpropionic acid in a dissolving solvent.

The term "precipitating solvent" is meant to describe a solvent that is capable of precipitating a compound dissolved in a solution. As used herein, precipitating solvent describes a solvent that precipitates amorphous rapamycin 42-ester with 3-hydroxy-2-(hydroxymethyl)-2-methylpropionic acid from a dissolving solvent. Precipitating solvents can include solvents that are miscible with the dissolving solvent containing the dissolved compound. Alternatively, the precipitating solvent can include a solvent that is immiscible with the dissolving solvent containing the dissolved compound. In one embodiment, the precipitating solvent is water. In another embodiment, the precipitating solvent is an alkane. One example of a suitable alkane is n-heptane. However, other suitable alkanes or combinations of any of the above-noted individual precipitating solvents can be selected.

The term "evaporation" is meant to describe a process by which a solid form of a compound is formed by evaporating a solvent from a solution.

The term "grinding" is meant to describe a process by which a solid form of a compound is ground using techniques known to those of skill in the art and include the techniques set forth in R. W. Lee et al., Particle Size Reduction in "Water Insoluble Drug Formulation", Rong Liu, Ed., Interpharm Press Co., Denver, Co.: 473-392 (2000). As used herein, grinding describes the process of grinding crystalline rapamycin 42-ester with 3-hydroxy-2-(hydroxymethyl)-2-methylpropionic acid to produce amorphous rapamycin 42-ester with 3-hydroxy-2-(hydroxymethyl)-2-methylpropionic acid using apparatuses known in the art, including grinding jars, among others. However, the type of grinding apparatus is not a limitation on the present invention.

The term "room temperature" is meant to describe a temperature of about 23 to about 25° C. However, one of skill in the art would readily understand that the specific room temperature can vary depending upon the conditions utilized during the formation of the amorphous form and environmental conditions.

The term "stable" as used herein is meant to describe a compound that decomposes less than about 10% over extended periods of time. In one embodiment, the term stable describes a compound that decomposes less than about 6%. In another embodiment, the term stable describes a compound that decomposes less than about 3%. In a further embodiment, the term stable describes a compound which decomposes less than about 0.7%. In yet another embodiment, the term stable describes a compound which decomposes less than about 0.4%.

The term "extended period of time" as used herein refers to a period of at least 1 or 2 weeks, during which the compounds of the invention are stable. Desirably, the compounds of the invention are stable for about 6 to about 12 months. However, one of skill in the art would readily be able to determine the period of time during which the compounds of the invention are stable.

II. Methods of Preparing Amorphous Rapamycin 42-Ester with 3-Hydroxy-2-(Hydroxymethyl)-2-Methylpropionic Acid In one aspect, the present invention provides methods for preparing amorphous rapamycin 42-ester with 3-hydroxy-2-(hydroxymethyl)-2-methylpropionic acid. Typically, the amorphous form is prepared from crystalline rapamycin 42-ester with 3-hydroxy-2-(hydroxymethyl)-2-methylpropionic acid. Such processes include evaporation, precipitation, and grinding, among other techniques. However, the particular process utilized to produce amorphous rapamycin 42-ester with 3-hydroxy-2-(hydroxymethyl)-2-methylpropionic acid is not a limitation on the present invention.

(A) Evaporation

According to the present invention, amorphous rapamycin 42-ester with 3-hydroxy-2-(hydroxymethyl)-2-methylpropionic acid can be prepared by evaporating a dissolving solvent from a solution containing rapamycin 42-ester with 3-hydroxy-2-(hydroxymethyl)-2-methylpropionic acid and a dissolving solvent.

Crystalline rapamycin 42-ester with 3-hydroxy-2-(hydroxymethyl)-2-methylpropionic acid is combined with a dissolving solvent to form a solution containing dissolved crystalline rapamycin 42-ester with 3-hydroxy-2-(hydroxymethyl)-2-methylpropionic acid. The dissolving solvent is typically an alcohol or an ether and can be dehydrated or may contain water. For example, suitable alcohols include ethanol, methanol, and isopropanol. In one particularly desirable embodiment, the dissolving solvent is ethanol. In another particularly desirable embodiment, the dissolving solvent is diethyl ether.

Other components are optionally added to the solution containing dissolving solvent and the crystalline form prior to evaporation, such as compounds which prevent decomposition of rapamycin 42-ester with 3-hydroxy-2-(hydroxymethyl)-2-methylpropionic acid. For example, antioxidants and stabilizers can be added to the solution containing dissolving solvent and the crystalline form. In one embodiment, antioxidants that can be added to the solution include butylated hydroxyanisole and butylated hydroxytoluene, among others. In another embodiment, stabilizers that can be added to the solution include ethylenediamine acetic acid, ascorbyl palmitate, and vitamin E.

After addition of the crystalline rapamycin 42-ester with 3-hydroxy-2-(hydroxymethyl)-2-methylpropionic acid, and optional other components, to the dissolving solvent, the solution is mixed for at least about 1 minute. Typically, the solution is mixed for about 1 minute to about 2 hours. One of skill in the art would readily be able to determine the type of mixing employed as well as the period of time required to mix the dissolving solvent with crystalline rapamycin 42-ester with 3-hydroxy-2-(hydroxymethyl)-2-methylpropionic acid.

The dissolving solvent is evaporated from the solution at or below temperatures that do not promote decomposition of the amorphous or crystalline forms. One of skill in the art would be able to determine the temperature necessary for evaporation based on the properties of the dissolving solvent. In one embodiment, the dissolving solvent is evaporated at a temperature of at least about 20° C. In a further embodiment, the dissolving solvent is evaporated at a temperature of about 25 to about 50° C. In another embodiment, the dissolving solvent is evaporated at a temperature of about 25 to about 30° C.

Vacuums can also be utilized to facilitate evaporation of the dissolving solvent. Vacuums having pressures of less than about 1 atmosphere (atm) are utilized in the present invention to evaporate the dissolving solvent. Alternatively, the dissolving solvent is evaporated from the solution at atmospheric pressures of about 1 atm. In one embodiment, evaporation is performed using pressures less than about 1 atm. In another embodiment, evaporation is performed using pressures obtained by the use of a rotavap and include vacuums of about 0.02 atm.

Vacuums can be maintained for short or longer periods of time in order to remove unwanted volatile compounds, including trapped or residual dissolving solvent or water. One of skill in the art would readily be able to determine the amount of time required to evaporate the trapped or residual dissolving solvent or water. In one embodiment, the vacuum is maintained for at least 8 hours. In another embodiment, the vacuum is maintained for about 8 hours to about 7 days.

Amorphous rapamycin 42-ester with 3-hydroxy-2-(hydroxymethyl)-2-methylpropionic acid is formed by evaporating an alcohol from a liquid sample containing crystalline rapamycin 42-ester with 3-hydroxy-2-(hydroxymethyl)-2-methylpropionic acid and the alcohol.

(B) Precipitation

In an alternative embodiment, amorphous rapamycin 42-ester with 3-hydroxy-2-(hydroxymethyl)-2-methylpropionic acid is obtained by precipitation. Specifically, the amorphous form is precipitated by adding a precipitating solvent to a solution containing crystalline rapamycin 42-ester with 3-hydroxy-2-(hydroxymethyl)-2-methylpropionic acid and a dissolving solvent.

Crystalline rapamycin 42-ester with 3-hydroxy-2-(hydroxymethyl)-2-methylpropionic acid is dissolved in a dissolving solvent. In one embodiment, the dissolving solvent is an alcohol or ether. In a further embodiment, the dissolving solvent is an alcohol. Such an alcohol can be a dehydrated alcohol or can contain water. Suitable alcohols can include ethanol, methanol, and isopropanol. In one particularly desirable embodiment, the dissolving solvent is ethanol. In another embodiment, the dissolving solvent can be an ether. In one particularly desirable embodiment, the ether is diethyl ether.

After addition of crystalline rapamycin 42-ester with 3-hydroxy-2-(hydroxymethyl)-2-methylpropionic acid to the dissolving solvent, the solution is mixed for at least about 1 minute. Typically, the solution is mixture for about 1 minute to about 2 hours. One of skill in the art would readily be able to determine the type of mixing employed as well as the period of time required to mix the dissolving solvent with crystalline rapamycin 42-ester with 3-hydroxy-2-(hydroxymethyl)-2-methylpropionic acid.

After a suitable period of time, the amorphous form is precipitated from the solution using a precipitating solvent. The amorphous form is typically insoluble in the precipitating solvent or insoluble in the dissolving solvent/precipitating solvent mixture at the temperature utilized during precipitation.

One of skill in the art would readily be able to determine the precipitating solvent necessary to precipitate amorphous rapamycin 42-ester with 3-hydroxy-2-(hydroxymethyl)-2-methylpropionic acid from the dissolving solvent depending upon the particular temperature, pressure, and dissolving solvent(s) utilized. However, any one of the above-noted precipitating solvents can be utilized in the present invention.

The amorphous form is thereby precipitated from the sample at, or below, a temperature that permits precipitation of the amorphous form. One of skill in the art would be able to determine the particular temperature required to facilitate precipitation of the amorphous form and taking into consideration the particular dissolving solvent and precipitating solvent utilized. In one embodiment, precipitation is performed at a temperature at or below about 50° C. In another embodiment, precipitation is performed at a temperature at or below about room temperature. In a further embodiment, precipitation is performed at a temperature of about 5° C.

Once formed, amorphous rapamycin 42-ester with 3-hydroxy-2-(hydroxymethyl)-2-methylpropionic acid can be isolated using techniques known to those of skill in the art and include filtration, decanting, centrifugation and chromatography, among others. Typically, filtration is utilized to isolate the precipitated amorphous sample.

Once precipitated, vacuums can be utilized to remove residual or trapped volatile compounds, including residual or trapped dissolving solvent or water. Vacuums having pressures of less than about 1 atmosphere (atm) can be utilized in the present invention. Preferably, vacuums of about 0.2 to about 0.8 atm are utilized.

Such vacuums can be maintained for short or longer periods of time. One of skill in the art would readily be able to determine the amount of time required to evaporate any residual or trapped dissolving solvent or water. In one embodiment, the vacuum is maintained for at least about 8 hours. In another embodiment, the vacuum is maintained for at least about 2 days. In a further embodiment, the vacuum is maintained for about 2 days to about 7 days.

The vacuums can be maintained at temperatures to promote removal of any residual or trapped dissolving solvent or water. In one embodiment, temperatures of about room temperature can be utilized. In another embodiment, temperatures of about 5° C. to about 25° C. can be utilized.

Amorphous rapamycin 42-ester with 3-hydroxy-2-(hydroxymethyl)-2-methylpropionic acid is therefore obtained by precipitating the amorphous form from a liquid sample using a precipitating solvent, wherein the liquid sample contains crystalline rapamycin 42-ester with 3-hydroxy-2-(hydroxymethyl)-2-methylpropionic acid and a dissolving solvent.

(C) Grinding

In yet a further aspect, amorphous rapamycin 42-ester with 3-hydroxy-2-(hydroxymethyl)-2-methylpropionic acid can be obtained by grinding crystalline rapamycin 42-ester with 3-hydroxy-2-(hydroxymethyl)-2-methylpropionic acid.

Several apparatuses can be utilized for grinding crystalline rapamycin 42-ester with 3-hydroxy-2-(hydroxymethyl)-2-methylpropionic acid and can be selected by one of skill of the art. Such apparatuses can include grinding jars, ball mills, and fluid energy mills, among others. One of skill in the art would readily be able to determine suitable grinding apparatuses and conditions for use in the present invention. However, the use of the particular grinding apparatus is not a limitation on the present invention.

Typically, crystalline rapamycin 42-ester with 3-hydroxy-2-(hydroxymethyl)-2-methylpropionic acid is placed in a grinding jar and the crystalline form ground. The amount of grinding time will depend on the amount of crystalline rapamycin 42-ester with 3-hydroxy-2-(hydroxymethyl)-2-methylpropionic acid placed in the grinding jar and the particular grinding jar utilized. Without wishing to be bound by theory, the inventors have discovered that as the grinding progresses over time, the amount of amorphous rapamycin 42-ester with 3-hydroxy-2-(hydroxymethyl)-2-methylpropionic acid increases. In one embodiment, crystalline rapamycin 42-ester with 3-hydroxy-2-(hydroxymethyl)-2-methylpropionic acid can be ground for at least about 20 minutes. In another embodiment, the crystalline form is ground for at least about 40 minutes. In a further embodiment, the crystalline form is ground for at least about 60 minutes.

Amorphous rapamycin 42-ester with 3-hydroxy-2-(hydroxymethyl)-2-methylpropionic acid can be obtained by grinding crystalline rapamycin 42-ester with 3-hydroxy-2-(hydroxymethyl)-2-methylpropionic acid.

III. Characterization of Amorphous Rapamycin 42-Ester with 3-Hydroxy-2-(Hydroxymethyl)-2-Methylpropionic Acid Characterization of amorphous rapamycin 42-ester with 3-hydroxy-2-(hydroxymethyl)-2-methylpropionic acid and distinguishing the same from crystalline rapamycin 42-ester with 3-hydroxy-2-(hydroxymethyl)-2-methylpropionic acid is accomplished using techniques known to those of skill in the art. Specifically, verification that rapamycin 42-ester with 3-hydroxy-2-(hydroxymethyl)-2-methylpropionic acid is present after evaporation, precipitation, or grinding can be performed using techniques including melting point, infrared spectroscopy (IR), nuclear magnetic resonance spectroscopy (NMR), mass spectral analysis (MS), combustion analysis, Raman spectroscopy, elemental analysis, and chromatography including high performance liquid chromatography.

The amorphous nature of rapamycin 42-ester with 3-hydroxy-2-(hydroxymethyl)-2-methylpropionic acid can also be confirmed using techniques utilized by those of skill in the art and include differential scanning calorimetry (DSC) and X-ray diffraction (XRD).

(A) Identification Using Spectroscopy

HPLC can be utilized to verify that the product obtained by evaporation, precipitation, or grinding as noted above is rapamycin 42-ester with 3-hydroxy-2-(hydroxymethyl)-2-methylpropionic acid. Specifically, the HPLC chromatograph of the amorphous sample should be substantially similar to the HPLC chromatograph of the crystalline form. Desirably, the HPLC chromatograph of the amorphous form is identical to the HPLC chromatograph of the crystalline form.

The HPLC chromatograph of the amorphous form can also contain additional peaks that correspond to impurities that can be readily identified by one of skill in the art. However, one of skill in the art would readily understand that the presence of impurities does not interfere with identification of the amorphous form.

A variety of HPLC conditions is utilized to obtain the HPLC chromatograph and can readily be determined by one of skill in the art and is not a limitation on the present invention. Such HPLC conditions include variations in the column temperature, flow rate, detection wavelength, column type, column size, and mobile phase, among others. In one embodiment, the HPLC conditions include a temperature of about 45° C., a flow rate of about 1.0 millimeter (mL)/minute, a detection wavelength of about 280 nanometers (nm), and a reverse phase 150 millimeter (mm)×4.6 mm YMC PACK® ODS-AM column containing 3 micron (μ) ODS particles. A variety of mobile phases can also be utilized in the present invention to obtain an HPLC chromatograph of the amorphous form. In one embodiment, the mobile phase includes an ammonium acetate solution, acetonitrile, dioxane, or a combination thereof. In one embodiment, the mobile phase includes a solution containing an ammonium acetate solution at a pH of about 3.8, acetonitrile, and dioxane at a molar ratio of about 80:52:68. In another embodiment, the mobile phase includes a solution having an ammonium acetate solution at a pH of about 3.8, acetonitrile, and dioxane at a molar ratio of about 20:34:46. Combinations of the above-noted mobile phases can also be utilized.

The HPLC chromatograph for amorphous rapamycin 42-ester with 3-hydroxy-2-(hydroxymethyl)-2-methylpropionic acid is therefore obtained and compared to a known HPLC chromatograph of the crystalline form. Typically, crystalline rapamycin 42-ester with 3-hydroxy-2-(hydroxymethyl)-2-methylpropionic acid has a retention time of about 21 minutes using the conditions noted above.

By using the HPLC conditions as noted above, the HPLC chromatograph of amorphous rapamycin 42-ester with 3-hydroxy-2-(hydroxymethyl)-2-methylpropionic acid was obtained. A retention time of about 21 minutes was obtained for the amorphous form. The HPLC chromatograph of the amorphous form is then compared to a HPLC of the crystalline form using the same HPLC conditions. In the present invention, the retention time for the amorphous form was identical to the retention time of about 21 minutes for the crystalline form.

After verification that rapamycin 42-ester with 3-hydroxy-2-(hydroxymethyl)-2-methylpropionic acid was present after evaporation, precipitation, or grinding, the amorphous nature of the same was confirmed using XRD and DSC.

(B) Identification Using X-Ray Diffraction

X-ray diffraction (XRD) techniques are utilized to distinguish amorphous forms from crystalline forms. As known to those of skill in the art, crystalline compounds produce XRD patterns containing sharp peaks. Amorphous compounds however generally produce XRD patterns containing broad and poorly defined peaks. Typically, powder XRD diffraction techniques are utilized to identify amorphous compounds.

XRD was therefore utilized in the present invention to distinguish amorphous rapamycin 42-ester with 3-hydroxy-2-(hydroxymethyl)-2-methylpropionic acid from the crystalline form. The powder XRD pattern of crystalline rapamycin 42-ester with 3-hydroxy-2-(hydroxymethyl)-2-methylpropionic acid was obtained in the present invention, but is also readily available to those of skill in the art. See, the XRD pattern and/or data for crystalline rapamycin 42-ester with 3-hydroxy-2-(hydroxymethyl)-2-methylpropionic acid in FIG. 1A. As known to those skilled in the art, a typical powder XRD pattern of the crystalline form contains several sharp peaks of varying intensity at about 8°, about 9°, about 11°, about 15°, about 16°, about 18°, about 19°, and about 20°.

The powder XRD pattern of amorphous rapamycin 42-ester with 3-hydroxy-2-(hydroxymethyl)-2-methylpropionic acid obtained as described herein is therefore obtained using X-ray crystallographic techniques known to those of skill in the art. In one embodiment, the XRD pattern of amorphous rapamycin 42-ester with 3-hydroxy-2-(hydroxymethyl)-2-methylpropionic acid includes one broad peak or halo. In another embodiment, the XRD pattern of the amorphous form contains one broad halo. In a further embodiment, the XRD pattern of the amorphous form contains one broad halo at 2θ of about 17°.

Other peaks can also be present in the XRD pattern of amorphous rapamycin 42-ester with 3-hydroxy-2-(hydroxymethyl)-2-methylpropionic acid and correspond to impurities in the sample. The other peaks typically correspond to minor amounts of crystalline rapamycin 42-ester with 3-hydroxy-2-(hydroxymethyl)-2-methylpropionic acid still present in the sample.

In addition to characterizing the amorphous form, XRD is used to monitor the formation of amorphous rapamycin 42-ester with 3-hydroxy-2-(hydroxymethyl)-2-methylpropionic acid. Typically, samples are obtained at various stages during evaporation, precipitation, and grinding and the XRD patterns obtained therefrom. In one embodiment, samples are withdrawn at various stages during grinding and the XRD pattern of the same obtained. In another embodiment, samples in dissolving solvent are withdrawn at various intervals, amorphous rapamycin 42-ester with 3-hydroxy-2-(hydroxymethyl)-2-methylpropionic acid solid precipitated, and the XRD diffraction patterns of the same obtained. In a further embodiment, samples in dissolving solvent are withdrawn at various intervals, the dissolving solvent evaporated, and the XRD diffraction pattern of the amorphous rapamycin 42-ester with 3-hydroxy-2-(hydroxymethyl)-2-methylpropionic acid obtained.

The inventors have discovered that the 2θ peaks of the XRD patterns of samples obtained after grinding crystalline rapamycin 42-ester with 3-hydroxy-2-(hydroxymethyl)-2-methylpropionic acid decrease in intensity over time as the crystalline rapamycin 42-ester with 3-hydroxy-2-(hydroxymethy)-2-methylpropionic acid is ground.

(C) Identification Using Differential Scanning Calorimetry

Differential scanning calorimetry (DSC) techniques are also utilized to distinguish amorphous rapamycin 42-ester with 3-hydroxy-2-(hydroxymethyl)-2-methylpropionic acid from the crystalline form. One of skill in the art would readily be able to determine the conditions necessary to obtain a DSC thermogram. A variety of DSC thermographs are available by those of skill in the art and include the TA differential scanning calorimeter, dry nitrogen gas as the purge gas, and a temperature increase at a rate of 5° C./min., among other instruments and conditions.

The DSC thermogram of crystalline rapamycin 42-ester with 3-hydroxy-2-(hydroxymethyl)-2-methylpropionic acid is known to those of skill in the art and is characterized by a sharp melting endotherm at about 164° C., thereby illustrating the crystalline nature of the compound. The DSC thermogram of the crystalline form can also include peaks that correspond to degradation products and include endotherms at about 173° to about 178° C.

The DSC thermograms of amorphous rapamycin 42-ester with 3-hydroxy-2-(hydroxymethyl)-2-methylpropionic acid prepared according to the present invention by evaporation, precipitation, and grinding lack the endotherm peak of about 164° C. which is present in the XRD pattern for the crystalline form. The lack of this peak confirms the amorphous nature of the sample. The DSC thermogram of the amorphous form prepared by evaporation and precipitation can also include degradation endotherms at about 43° C., 105° C., 173° C. and 176-177° C. Without wishing to be bound by theory, the endotherm at 43° C. corresponds to residual dissolving solvent, typically ethanol and/or water.

The DSC thermogram of amorphous rapamycin 42-ester with 3-hydroxy-2-(hydroxymethyl)-2-methylpropionic acid prepared by precipitation also includes an exotherm at about 109° C.

The DSC thermogram of the amorphous form prepared by grinding can include endotherms at about 52° C., 105° C., 155° C., and 173-177° C. and an exotherm at about 127° C. Without wishing to be bound by theory, the inventors have determined that the endotherms at 176-177° correspond to degradation product. The inventors have also determined that as the grinding progresses, the melting point of amorphous rapamycin 42-ester with 3-hydroxy-2-(hydroxymethyl)-2-methylpropionic acid corresponding to the endotherm at 164° C. shifts to 155° C.

In one embodiment, amorphous rapamycin 42-ester with 3-hydroxy-2-(hydroxymethyl)-2-methylpropionic acid can therefore be prepared having an X-ray diffraction peak pattern containing a broad halo at 2θ of about 17°, a differential scanning calorimetry thermogram lacking the endotherm peak of about 164° for crystalline rapamycin 42-ester with 3-hydroxy-2-(hydroxymethyl)-2-methylpropionic acid, and a high performance liquid chromatography chromatograph characteristic of rapamycin 42-ester with 3-hydroxy-2-(hydroxymethyl)-2-methylpropionic acid.

IV. Solubility of Amorphous Rapamycin 42-Ester with 3-Hydroxy-2-(Hydroxymethyl)-2-Methylpropionic Acid Amorphous rapamycin 42-ester with 3-hydroxy-2-(hydroxymethyl)-2-methylpropionic acid prepared according to the present invention has several advantages over the crystalline form. In one aspect, amorphous rapamycin 42-ester with 3-hydroxy-2-(hydroxymethyl)-2-methylpropionic acid has a higher solubility than the crystalline form.

Solid rapamycin 42-ester with 3-hydroxy-2-(hydroxymethyl)-2-methylpropionic acid, whether in crystalline or amorphous form, is added to dissolving solvents for dissolution. In one embodiment, amorphous rapamycin 42-ester with 3-hydroxy-2-(hydroxymethyl)-2-methylpropionic acid is obtained as a solid by evaporation, precipitation, or grinding as noted above, and optionally is pressed through a screen to further reduce the size of the particles of the solid.

As is known to those skilled in the art, micronization is also useful for finely grinding or reducing the size of the particles of a solid. Amorphous rapamycin 42-ester with 3-hydroxy-2-(hydroxymethyl)-2-methylpropionic acid can be micronized using techniques known to one skilled in the art. One of skill in the art would readily be able to select an apparatus for micronization and include jet mills, among others. Examples of jet mills known in the art include TROST™ mills, MC JETMILL® energy mills, and ALPINE™ AS spiral jet mills, among others.

The solubility of amorphous rapamycin 42-ester with 3-hydroxy-2-(hydroxymethyl)-2-methylpropionic acid can be measured by dissolving separate samples of the crystalline and amorphous forms in a dissolving solvent. The solubility of these samples can then be compared. A variety of solvents can be utilized to determine the solubility of amorphous and can be selected by one of skill in the art. In one embodiment, the solvent dissolves one or both of amorphous and crystalline rapamycin 42-ester with 3-hydroxy-2-(hydroxymethyl)-2-methylpropionic acid. In a further embodiment, the solvent is water. In another embodiment, the solvent is a solution containing water and citric acid. In yet a further embodiment, the solvent is a solution containing water, citric acid, and ethylenediaminetetraacetic acid (EDTA) or sodium lauryl sulfate (SLS). In yet another embodiment, the solvent is a 0.005 M water and citric acid solution adjusted to a pH of about 4.6. In yet a further embodiment, the solvent is a citrate buffer containing EDTA, optionally adjusted to a pH of about 4.6. In another embodiment, the solvent is a citrate buffer containing 0.2% SLS.

The solubility of amorphous rapamycin 42-ester with 3-hydroxy-2-(hydroxymethyl)-2-methylpropionic acid can also be increased by increasing the periods of time mixing the crystalline form in the dissolving solvent or by grinding the same. One of skill in the art would readily understand the amount of time required to facilitate dissolution of amorphous rapamycin 42-ester with 3-hydroxy-2-(hydroxymethyl)-2-methylpropionic acid in the dissolving solvent. In one embodiment, amorphous rapamycin 42-ester with 3-hydroxy-2-(hydroxymethyl)-2-methylpropionic acid is dissolved in a solvent for at least about 0.5 hours. In another embodiment, amorphous rapamycin 42-ester with 3-hydroxy-2-(hydroxymethyl)-2-methylpropionic acid is dissolved in a solvent for about 0.5 hours to about 72 hours. In a further embodiment, amorphous rapamycin 42-ester with 3-hydroxy-2-(hydroxymethyl)-2-methylpropionic acid is dissolved in a solvent for about 24 to about 48 hours.

Samples of amorphous rapamycin 42-ester with 3-hydroxy-2-(hydroxymethyl)-2-methylpropionic acid can also be compressed into tablets, as discussed in detail below. Such tablets containing the same show a greater rate of dissolution than tablets containing crystalline rapamycin 42-ester with 3-hydroxy-2-(hydroxymethyl)-2-methylpropionic acid (FIG. 1). In one embodiment, tablets containing amorphous rapamycin 42-ester with 3-hydroxy-2-(hydroxymethyl)-2-methylpropionic acid are about 1.5 times more soluble than tablets containing the crystalline form.

Typically, amorphous rapamycin 42-ester with 3-hydroxy-2-(hydroxymethyl)-2-methylpropionic acid is stable at temperatures of up to about 5° C.

V. Compositions Containing Amorphous Rapamycin 42-Ester with 3-Hydroxy-2-(Hydroxymethyl)-2-Methylpropionic Acid Compositions containing amorphous rapamycin 42-ester with 3-hydroxy-2-(hydroxymethyl)-2-methylpropionic acid can also be prepared according to the present invention. Such compositions are prepared by combining amorphous rapamycin 42-ester with 3-hydroxy-2-(hydroxymethyl)-2-methylpropionic acid and a pharmaceutically acceptable carrier.

The compositions described herein containing amorphous rapamycin 42-ester with 3-hydroxy-2-(hydroxymethyl)-2-methylpropionic acid can be formulated in any form suitable for the desired route of delivery using a pharmaceutically effective amount of amorphous rapamycin 42-ester with 3-hydroxy-2-(hydroxymethyl)-2-methylpropionic acid. For example, the compositions of the invention can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral.

The oral dosage tablet composition of this invention can also be used to make oral dosage tablets containing derivatives of amorphous rapamycin 42-ester with 3-hydroxy-2-(hydroxymethyl)-2-methylpropionic acid, including, but not limited to, esters, carbamates, sulfates, ethers, oximes, carbonates, and the like which are known to those of skill in the art.

A pharmaceutically effective amount of amorphous rapamycin 42-ester with 3-hydroxy-2-(hydroxymethyl)-2-methylpropionic acid can vary depending on the specific compound(s), mode of delivery, severity of the condition being treated, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. However, daily dosages can be lowered or raised based on the periodic delivery.

Amorphous rapamycin 42-ester with 3-hydroxy-2-(hydroxymethyl)-2-methylpropionic acid can be combined with one or more pharmaceutically acceptable carriers or excipients including, without limitation, solid and liquid carriers which are compatible with the compositions of the present invention. Such carriers include adjuvants, syrups, elixirs, diluents, binders, lubricants, surfactants, granulating agents, disintegrating agents, emollients, metal chelators, pH adjustors, surfactants, fillers, disintegrants, and combinations thereof, among others. In one embodiment, amorphous rapamycin 42-ester with 3-hydroxy-2-(hydroxymethyl)-2-methylpropionic acid is combined with metal chelators, pH adjustors, surfactants, fillers, disintegrants, lubricants, and binders.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Binders can include, without limitation, cellulose, methylcellulose, hydroxymethylcellulose, carboxymethylcellulose calcium, carboxymethylcellulose sodium, hydroxypropylcellulose, hydroxypropylmethylcellulose phthalate, microcrystalline cellulose, noncrystalline cellulose, polypropylpyrrolidone, polyvinylpyrrolidone (povidone, PVP), gelatin, gum arabic and acacia, polyethylene glycols, starch, sugars such as sucrose, kaolin, dextrose, and lactose, cholesterol, tragacanth, stearic acid, gelatin, casein, lecithin (phosphatides), cetostearyl alcohol, cetyl alcohol, cetyl esters wax, dextrates, dextrin, glyceryl monooleate, glyceryl monostearate, glyceryl palmitostearate, polyoxyethylene alkyl ethers, polyoxyethylene castor oil derivatives, polyoxyethylene stearates, polyvinyl alcohol, and gelatin, among others. In one embodiment, the binder is povidone, hydroxypropylmethylcellulose, carboxymethylcellulose, or gelatin. In another embodiment, the binder is povidone.

Lubricants can include magnesium stearate, light anhydrous silicic acid, talc, stearic acid, sodium lauryl sulfate, and sodium stearyl furamate, among others. In one embodiment, the lubricant is magnesium stearate, stearic acid, or sodium stearyl furamate. In another embodiment, the lubricant is magnesium stearate.

Granulating agents can include, without limitation, silicon dioxide, microcrystalline cellulose, starch, calcium carbonate, pectin, crospovidone, and polyplasdone, among others.

Disintegrating agents or disintegrants can include croscarmellose sodium, starch, carboxymethylcellulose, substituted hydroxypropylcellulose, sodium bicarbonate, calcium phosphate, calcium citrate, sodium starch glycolate, pregelatinized starch or crospovidone, among others. In one embodiment, the disintegrant is croscarmellose sodium.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include polysorbates, sorbitan esters, poloxamer, or sodium lauryl sulfate. In one embodiment, the surfactant is sodium lauryl sulfate.

Metal chelators can include physiologically acceptable chelating agents including edetic acid, malic acid, or fumaric acid. In one embodiment, the metal chelator is edetic acid.

pH adjusters can also be utilized to adjust the pH of a solution containing rapamycin 42-ester with 3-hydroxy-2-(hydroxymethyl)-2-methylpropionic acid to about 4 to about 6. In one embodiment, the pH of a solution containing rapamycin 42-ester with 3-hydroxy-2-(hydroxymethyl)-2-methylpropionic acid is adjusted to a pH of about 4.6. pH adjustors can include physiologically acceptable agents including citric acid, ascorbic acid, fumaric acid, or malic acid, and salts thereof. In one embodiment, the pH adjuster is citric acid.

Fillers that can be used according to the present invention include anhydrous lactose, microcrystalline cellulose, mannitol, calcium phosphate, pregelatinized starch, or sucrose. In one embodiment, the filler is anhydrous lactose. In another embodiment, the filler is microcrystalline cellulose.

In one embodiment, compositions containing amorphous rapamycin 42-ester with 3-hydroxy-2-(hydroxymethyl)-2-methylpropionic acid are delivered orally by tablet, caplet or capsule, microcapsules, dispersible powder, granule, suspension, syrup, elixir, and aerosol. Desirably, when compositions containing amorphous rapamycin 42-ester with 3-hydroxy-2-(hydroxymethyl)-2-methylpropionic acid are delivered orally, delivery is by tablets and hard- or liquid-filled capsules.

In another embodiment, the compositions containing amorphous rapamycin 42-ester with 3-hydroxy-2-(hydroxymethyl)-2-methylpropionic acid can be delivered intravenously, intramuscularly, subcutaneously, parenterally and intraperitoneally in the form of sterile injectable solutions, suspensions, dispersions, and powders which are fluid to the extent that easy syringe ability exits. Such injectable compositions are sterile and stable under conditions of manufacture and storage, and free of the contaminating action of microorganisms such as bacteria and fungi.

In a further embodiment, compositions containing amorphous rapamycin 42-ester with 3-hydroxy-2-(hydroxymethyl)-2-methylpropionic acid can be delivered rectally in the form of a conventional suppository.

In another embodiment, compositions containing amorphous rapamycin 42-ester with 3-hydroxy-2-(hydroxymethyl)-2-methylpropionic acid can be delivered vaginally in the form of a conventional suppository, cream, gel, ring, or coated intrauterine device (IUD).

In yet another embodiment, compositions containing amorphous rapamycin 42-ester with 3-hydroxy-2-(hydroxymethyl)-2-methylpropionic acid can be delivered intranasally or intrabronchially in the form of an aerosol.

It is also contemplated that compositions of this invention containing amorphous rapamycin 42-ester with 3-hydroxy-2-(hydroxymethyl)-2-methylpropionic acid can be co-administered with one or more other agents including anti-rejection chemotherapeutic agents.

The dosage requirements of amorphous rapamycin 42-ester with 3-hydroxy-2-(hydroxymethyl)-2-methylpropionic acid can vary depending on the severity of the symptoms presented and the particular subject being treated. One of skill in the art would readily be able to determine the amount of amorphous rapamycin 42-ester with 3-hydroxy-2-(hydroxymethyl)-2-methylpropionic acid required. In one embodiment, about 0.5 to about 75 mg is administered. In a further embodiment, about 1 to about 25 mg is administered. In another embodiment, about 0.5 to about 10 mg is administered, particularly when used in combination with another agent. In yet a further embodiment, about 2 to about 5 mg is administered. In yet another embodiment, about 5 to about 15 mg is administered.

Treatment can be initiated with dosages of amorphous rapamycin 42-ester with 3-hydroxy-2-(hydroxymethyl)-2-methylpropionic acid smaller than those required to produce a desired effect and generally less than the optimum dose of amorphous rapamycin 42-ester with 3-hydroxy-2-(hydroxymethyl)-2-methylpropionic acid. Thereafter, the dosage can be increased until the optimum effect under the circumstances is reached. Precise dosages will be determined by the administering physician based on experience with the individual subject being treated. In general, the compositions of this invention are most desirably administered at a concentration that will generally afford effective results without causing any harmful or deleterious side effects.

VI. Methods of Preparing Administrable Compositions Containing Amorphous Rapamycin 42-Ester with 3-Hydroxy-2-(Hydroxymethyl)-2-Methylpropionic Acid In one aspect, the present invention includes methods of preparing a pharmaceutical composition containing amorphous rapamycin 42-ester with 3-hydroxy-2-(hydroxymethyl)-2-methylpropionic acid. The composition can be administered to a mammalian subject by several different routes as noted above and is desirably administered orally in solid or liquid form.

Solid forms, including tablets, capsules, and caplets, containing amorphous rapamycin 42-ester with 3-hydroxy-2-(hydroxymethyl)-2-methylpropionic acid can be formed by blending the amorphous form with one or more of the components described above. In one embodiment, the components of the composition are dry or wet blended. In another embodiment, the components are dry granulated. In a further embodiment, the components are suspended or dissolved in a liquid and added to a form suitable for administration to a mammalian subject.

Liquid forms containing amorphous rapamycin 42-ester with 3-hydroxy-2-(hydroxymethyl)-2-methylpropionic acid can be formed by dissolving or suspending the amorphous form in a liquid suitable for administration to a mammalian subject.

In one embodiment, methods of preparing a pharmaceutical composition containing amorphous rapamycin 42-ester with 3-hydroxy-2-(hydroxymethyl)-2-methylpropionic acid include combining amorphous rapamycin 42-ester with 3-hydroxy-2-(hydroxymethyl)-2-methylpropionic acid, a metal chelator, a pH adjuster, a surfactant, a filler, a binder, a disintegrant, and a lubricant.

In another embodiment, methods of preparing a pharmaceutical composition containing amorphous rapamycin 42-ester with 3-hydroxy-2-(hydroxymethyl)-2-methylpropionic acid include combining amorphous rapamycin 42-ester with 3-hydroxy-2-(hydroxymethyl)-2-methylpropionic acid, a metal chelator, a pH adjuster, a surfactant, a first portion of at least one filler, a binder, a first portion of a disintegrant, a second portion of at least one filler, a second portion of a disintegrant and a lubricant.

In a further embodiment, methods of preparing a pharmaceutical composition containing amorphous rapamycin 42-ester with 3-hydroxy-2-(hydroxymethyl)-2-methylpropionic acid include combining amorphous rapamycin 42-ester with 3-hydroxy-2-(hydroxymethyl)-2-methylpropionic acid, edetic acid, citric acid, sodium lauryl sulfate, anhydrous lactose, povidone, croscarmellose sodium, and magnesium stearate.

In yet another embodiment, methods of preparing a pharmaceutical composition containing amorphous rapamycin 42-ester with 3-hydroxy-2-(hydroxymethyl)-2-methylpropionic acid include combining amorphous rapamycin 42-ester with 3-hydroxy-2-(hydroxymethyl)-2-methylpropionic acid, edetic acid, citric acid, sodium lauryl sulfate, a first portion of anhydrous lactose, povidone, a first portion of croscarmellose sodium, a second portion of anhydrous lactose, a second portion of croscarmellose sodium, and magnesium stearate.

In yet another embodiment, methods of preparing a pharmaceutical composition containing amorphous rapamycin 42-ester with 3-hydroxy-2-(hydroxymethyl)-2-methylpropionic acid include the steps of (a) combining an amorphous form of rapamycin 42-ester with 3-hydroxy-2-(hydroxymethyl)-2-methylpropionic acid, a metal chelator, and a pH adjuster; (b) combining a surfactant, a first portion of at least one filler, a binder, and a first portion of a disintegrant; (c) combining the product of (b) with the product of (a); (d) combining a second portion of at least one filler and a second portion of a disintegrant with the product of (c); (e) blending the product of (d); and (f) combining the product of (e) with a lubricant. The product of step (b) can optionally be passed through a device for removing large clumps, for example a screen.

In yet a further embodiment, methods of preparing a pharmaceutical composition containing amorphous rapamycin 42-ester with 3-hydroxy-2-(hydroxymethyl)-2-methylpropionic acid include the steps of (a) combining an amorphous form of rapamycin 42-ester with 3-hydroxy-2-(hydroxymethyl)-2-methylpropionic acid, edetic acid, and citric acid; (b) combining sodium lauryl sulfate, a first portion of anhydrous lactose, povidone, and a first portion of croscarmellose sodium; (c) combining the product of (b) with the product of (a); (d) combining a second portion of anhydrous lactose and a second portion of croscarmellose sodium with the product of (c); (e) blending the product of (d); and (f) combining the product of (e) with magnesium stearate.

The present invention also provides kits or packages of pharmaceutical compositions designed for use in the present invention. Kits of the present invention can include an amorphous form of rapamycin 42-ester with 3-hydroxy-2-(hydroxymethyl)-2-methylpropionic acid and a carrier suitable for administration to a mammalian subject as discussed above.

VII. Methods of Using Amorphous Rapamycin 42-Ester with 3-Hydroxy-2-(Hydroxymethyl)-2-Methylpropionic Acid Amorphous rapamycin 42-ester with 3-hydroxy-2-(hydroxymethyl)-2-methylpropionic acid can be utilized in the treatment or prevention of a variety of conditions known to those of skill in the art that the crystalline form is known to treat or prevent.

Amorphous rapamycin 42-ester with 3-hydroxy-2-(hydroxymethyl)-2-methylpropionic acid can therefore possess immunosuppressive, antirejection, antifungal, anti-inflammatory, antitumor, and antiproliferative activities.

The amorphous form can therefore be used to treat or inhibit transplantation rejection including kidney, heart, liver, lung, bone marrow, pancreas, cornea, small bowel, skin allografts, and heart valve xenografts. The amorphous form can also be used to treat or inhibit allergic encephalomyelitis, arthritis, and hyperproliferative vascular disorders including restenosis, atherosclerosis, and cardiac inflammatory disease. Adult T-cell leukemia/lymphoma, graft vs. host disease, ocular inflammation, and fungal infections can also be treated using amorphous rapamycin 42-ester with 3-hydroxy-2-(hydroxymethyl)-2-methylpropionic acid. The amorphous form can further be used to treat or inhibit solid tumors including sarcomas and carcinomas including astrocytomas, prostate cancer, breast cancer, small cell lung cancer, and ovarian cancer. Autoimmune diseases including lupus, rheumatoid arthritis, diabetes mellitus, myasthenia gravis, and multiple sclerosis can also be treated or prevented using amorphous rapamycin 42-ester with 3-hydroxy-2-(hydroxymethyl)-2-methylpropionic acid prepared according to the present invention. Further, diseases of inflammation including psoriasis, dermatitis, eczema, seborrhea, inflammatory bowel disease, pulmonary inflammation including asthma, chronic obstructive pulmonary disease, emphysema, acute respiratory distress syndrome, bronchitis, and eye uveitis can also be treated or inhibited using the amorphous form of rapamycin 42-ester with 3-hydroxy-2-(hydroxymethyl)-2-methylpropionic acid.

Appropriate dosage regimens can be readily determined based upon the information provided herein.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Process for Preparing Amorphous Rapamycin 42-Ester with 3-Hydroxy-2-(Hydroxymethyl)-2-Methylpropionic Acid A. Process for Preparing Amorphous Rapamycin 42-ester with 3-hydroxy-2-(hydroxymethyl)-2-methylpropionic acid by Evaporation Using Butylated Hydroxy Toluene and Butylated Hydroxy Anisole Crystalline rapamycin 42-ester with 3-hydroxy-2-(hydroxymethyl)-2-methylpropionic acid (0.5 g), butylated hydroxytoluene (BHT) (0.063 g), and butylated hydroxyanisole (BHA) (0.125 g) were dissolved in dehydrated ethanol (15 mL). The alcohol was evaporated at reduced pressures using a rotavap and at a constant temperature of about 25 to about 30° C. by use of a water bath. The evaporated solid material (batch A1) was kept overnight under vacuum to remove residual ethanol The dried material was then passed through a #80 mesh screen and analyzed using X-ray diffraction (XRD) and differential scanning calorimetry (DSC).

B. Process for Preparing Amorphous Rapamycin 42-ester with 3-hydroxy-2-(hydroxymethyl)-2-methylpropionic acid by Evaporation Crystalline rapamycin 42-ester with 3-hydroxy-2-(hydroxymethyl)-2-methylpropionic acid (0.5 g) was dissolved in dehydrated ethanol (2 mL). The alcohol was then evaporated at reduced temperatures using a rotavap at a constant temperature of about 25 to about 30° C. using a water bath. The evaporated materials were maintained at reduced pressures overnight to remove residual ethanol.

The dried material (batch B1) was then passed through a #80 mesh screen and analyzed using XRD and DSC.

C. Process for Preparing Amorphous Rapamycin 42-ester with 3-hydroxy-2-(hydroxymethyl)-2-methylpropionic acid Varying amounts of crystalline rapamycin 42-ester with 3-hydroxy-2-(hydroxymethyl)-2-methylpropionic acid were dissolved in varying amounts of ethanol as set forth in Table 1. The resultant solutions were then kept at room temperature (batches C1-C3) or cooled to temperatures below room temperatures (batches C4 and C5) utilizing ice cold water at a temperature of about 0° C. for about 40 minutes. Water was added to each of these solutions and solids precipitated from the solutions. The precipitated solids were collected by filtration and dried at reduced pressures at room temperature for about 2 to about 7 days.

TABLE 1

| Batch No. | Batch size (g) | Temperature | Ethanol Volume (mL) | Water Volume (mL) | Yield (%) |
|---|---|---|---|---|---|
| C1 | 0.20 | Room Temp. | 4 | 20 | 75 |
| C2 | 1.00 | Room Temp. | 6 | 100 | Not determined |
| C3 | 1.00 | Room Temp. | 6 | 40 | 82 |
| C4 | 4.50 | 8° C. | 25 | 150 | 94 |
| C5 | 20.0 | 9° C. | 90 | 200 | 90 |

D. Process for Preparing Amorphous Rapamycin 42-ester with 3-hydroxy-2-(hydroxymethyl)-2-methylpropionic acid by Grinding Crystalline rapamycin 42-ester with 3-hydroxy-2-(hydroxymethyl)-2-methylpropionic acid (1.416 g) was ground in a RETSCH® Mixer Mill (Type MM2) with a 25 mL grinding jar and two stainless steel balls having diameters of 12 mm at a mill speed of 40 revolutions per minute (rpm). Ground samples were withdrawn for XRD and DSC analyses at 20 (batch D1), 40 (batch D2), and 60 minutes (batch D3).

Example 2

Micronization of Amorphous Rapamycin 42-Ester with 3-Hydroxy-2-(Hydroxymethyl)-2-Methylpropionic Acid Micronization of amorphous rapamycin 42-ester with 3-hydroxy-2-(hydroxymethyl)-2-methylpropionic acid (15.0 g) was performed using a TROST® mill (jet mill) at a nitrogen inlet pressure of about 40 pounds per square inch (psi), feed rate of about 1 g/min to give micronized amorphous rapamycin 42-ester with 3-hydroxy-2-(hydroxymethyl)-2-methylpropionic acid (10.3 g).

Example 3

Spectral Analysis of Amorphous Rapamycin 42-Ester with 3-Hydroxy-2-(Hydroxymethyl)-2-Methylpropionic Acid The HPLC chromatograph of amorphous rapamycin 42-ester with 3-hydroxy-2-(hydroxymethyl)-2-methylpropionic acid samples prepared by evaporation, precipitation, and grinding as noted in Example 1 were obtained.

The HPLC conditions included a column temperature of about 45° C., flow rate of about 1.0 mL/min, detection wavelength of about 280 nanometers (nm), 150 millimeters (mm)× 4.6 mm YMC Pack™ ODS-AM column containing 3μ particles, a first mobile phase containing an ammonium acetate solution at a pH of about 3.8, acetonitrile, and dioxane at a molar ratio of about 80:52:68, and a second mobile phase containing an ammonium acetate solution at a pH of about 3.8, acetonitrile, and dioxane at a molar ratio of about 20:34:46.

The HPLC chromatographs of the amorphous samples were compared with the HPLC chromatograph of a sample of crystalline rapamycin 42-ester with 3-hydroxy-2-(hydroxymethyl)-2-methylpropionic acid material using the same above-noted conditions. A retention time of about 21 min was observed for amorphous rapamycin 42-ester with 3-hydroxy-2-(hydroxymethyl)-2-methylpropionic acid material.

Example 4

Characterization of Amorphous Rapamycin 42-Ester with 3-Hydroxy-02-(Hydroxymethyl)-2-Methylpropionic Acid The XRD pattern and DSC thermograms were obtained for crystalline and amorphous rap amycin 42-ester with 3-hydroxy-2-(hydroxymethyl)-2-methylpropionic acid. The XRD patterns were obtained according to the present invention using a Phillips X'PERT™ BW-3040 commercially available X-Ray Diffraction instrument. The DSC thermograms were obtained according to the present invention using a commercially available Differential Scanning Calorimeter.

A. X-Ray Diffraction (XRD)

Figures 1A, 1B, 1C, 1D:
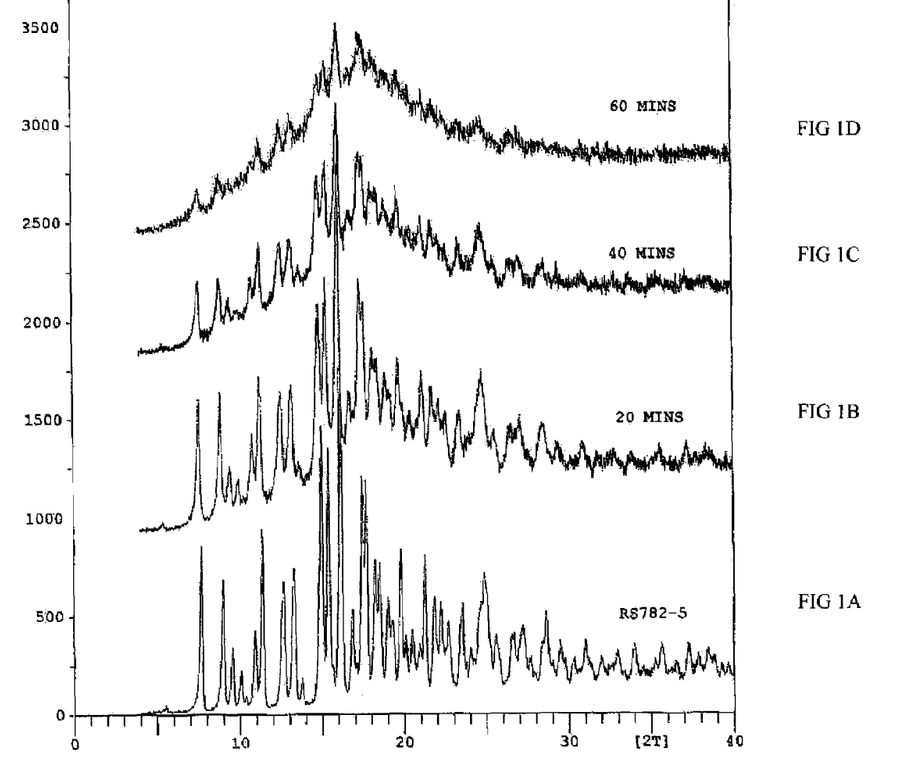
Figure 2:
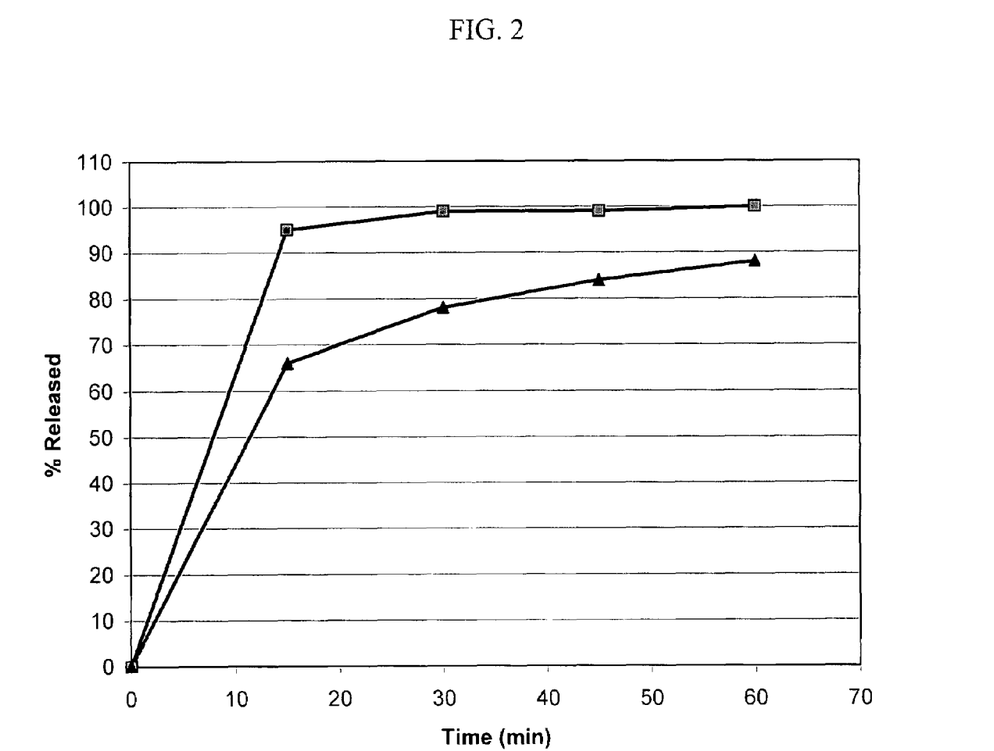
FIG. 2 is a graph comparing the rate of dissolution of tablets containing amorphous and crystalline rapamycin 42-ester with 3-hydroxy-2-(hydroxymethyl)-2-methylpropionic acid in a 0.4% sodium lauryl sulfate (SLS) solution. The tablets containing amorphous rapamycin 42-ester with 3-hydroxy-2-(hydroxymethyl)-2-methylpropionic acid are represented by squares and the tablets containing crystalline rapamycin 42-ester with 3-hydroxy-2-(hydroxymethyl)-2-methylpropionic acid are represented by triangles.

(i) Crystalline rapamycin 42-ester with 3-hydroxy-2-(hydroxymethyl)-2-methylpropionic acid The XRD pattern of crystalline rapamycin 42-ester with 3-hydroxy-2-(hydroxymethyl)-2-methylpropionic acid was obtained and displays characteristic peaks in the XRD pattern at 2θ at about 8°, about 9°, about 11°, about 15°, about 16°, about 17°, about 18°, and about 20° (FIG. 1A).

(ii) Amorphous rapamycin 42-ester with 3-hydroxy-2-(hydroxymethyl)-2-methylpropionic acid The XRD pattern of amorphous rapamycin 42-ester with 3-hydroxy-2-(hydroxymethyl)-2-methylpropionic acid prepared by evaporation and precipitation showed that the characteristic crystalline peaks for crystalline rapamycin 42-ester with 3-hydroxy-2-(hydroxymethyl)-2-methylpropionic acid same were not present in the X-ray diffraction pattern for the amorphous form.

Figure 3A:
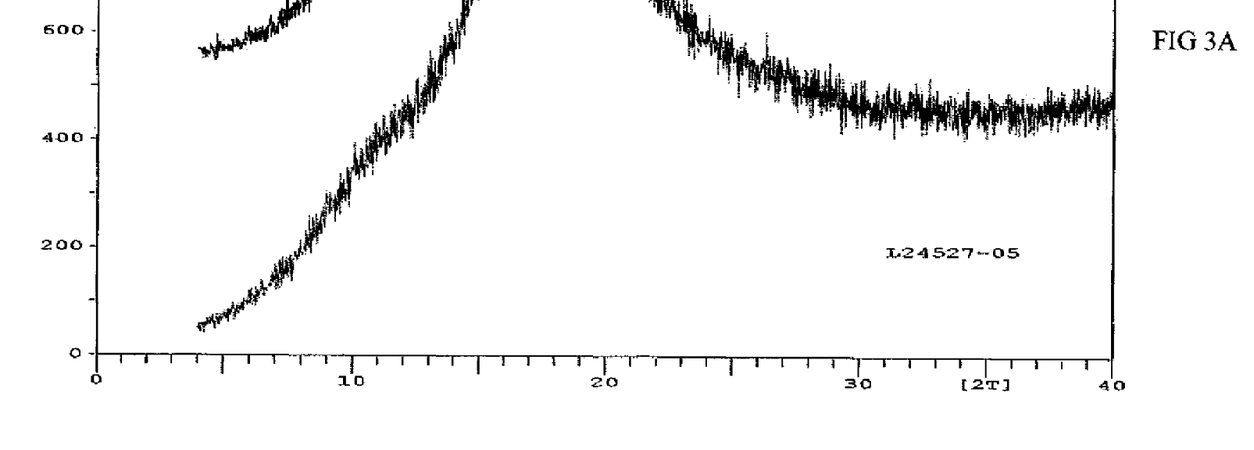
FIG. 3A is an XRD pattern of amorphous rapamycin 42-ester with 3-hydroxy-2-(hydroxymethyl)-2-methylpropionic acid prepared by evaporation.
Figure 3B:
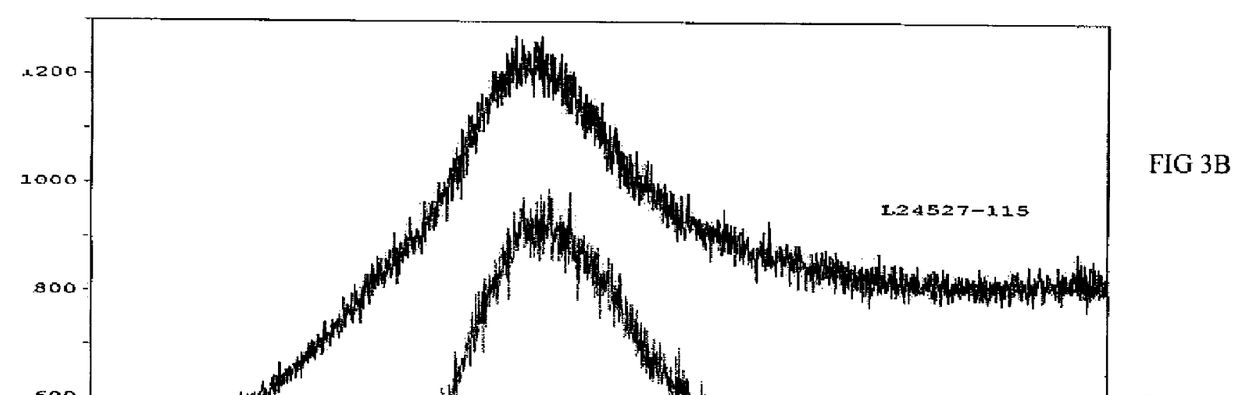
FIG. 3B is an XRD pattern of amorphous rapamycin 42-ester with 3-hydroxy-2-(hydroxymethyl)-2-methylpropionic acid prepared by precipitation.

Specifically, the XRD pattern of amorphous rapamycin 42-ester with 3-hydroxy-2-(hydroxymethyl)-2-methylpropionic acid prepared by solvent evaporation (batch A1) or precipitation (batch C1) showed a broad peak at 2θ of about 17° (FIGS. 3A and 3B).

Further, the XRD patterns of amorphous rapamycin 42-ester with 3-hydroxy-2-(hydroxymethyl)-2-methylpropionic acid prepared by grinding (batches D1-D3) showed a marked decrease in the characteristic crystalline peaks with increasing grinding time (FIGS. 1B-1D and Table 2). Specifically, as the grinding time increased, the peaks corresponding to crystalline rapamycin 42-ester with 3-hydroxy-2-(hydroxymethyl)-2-methylpropionic acid disappeared, thereby illustrating the formation of amorphous rapamycin 42-ester with 3-hydroxy-2-(hydroxymethyl)-2-methylpropionic acid.

TABLE 2

| Batch | X-ray Diffraction Peaks at 2θ (°) |
|---|---|
| crystalline | 7.8, 9.0, 9.8, 10.1, 11.0, 11.3, 12.7, 13.3, 14.8, 15.2, 16.0, 17.2, 17.6, 18.1, 18.3, 19.0, 19.8, 21.1, 21.8, 22.1, 23.5, 25.0, 25.6, 26.6, 27.1, and 28.5 |
| D1 | 7.8, 8.8, 9.7, 10.0, 10.8, 11.3, 12.5, 13.3, 15.0, 15.5, 16.2, 17.2, 18.2, 19.1, 19.9, 21.1, 22.0, 22.2, 23.6, 25.0, 26.7, 27.3, and 28.8 |
| D2 | 7.8, 9.0, 9.3, 10.8, 11.2, 12.8, 13.2, 15.0, 15.3, 16.0, 17.6, 18.2, 19.9, 21.1, and 24.9 |
| D3 | 8.0, 9.1, 11.2, 12.8, 13.7, 15.4, and 16.5 |
| A1 | 17 |
| C1 | 17 |

B. Differential Scanning Calorimetry (DSC)

Figure 4:
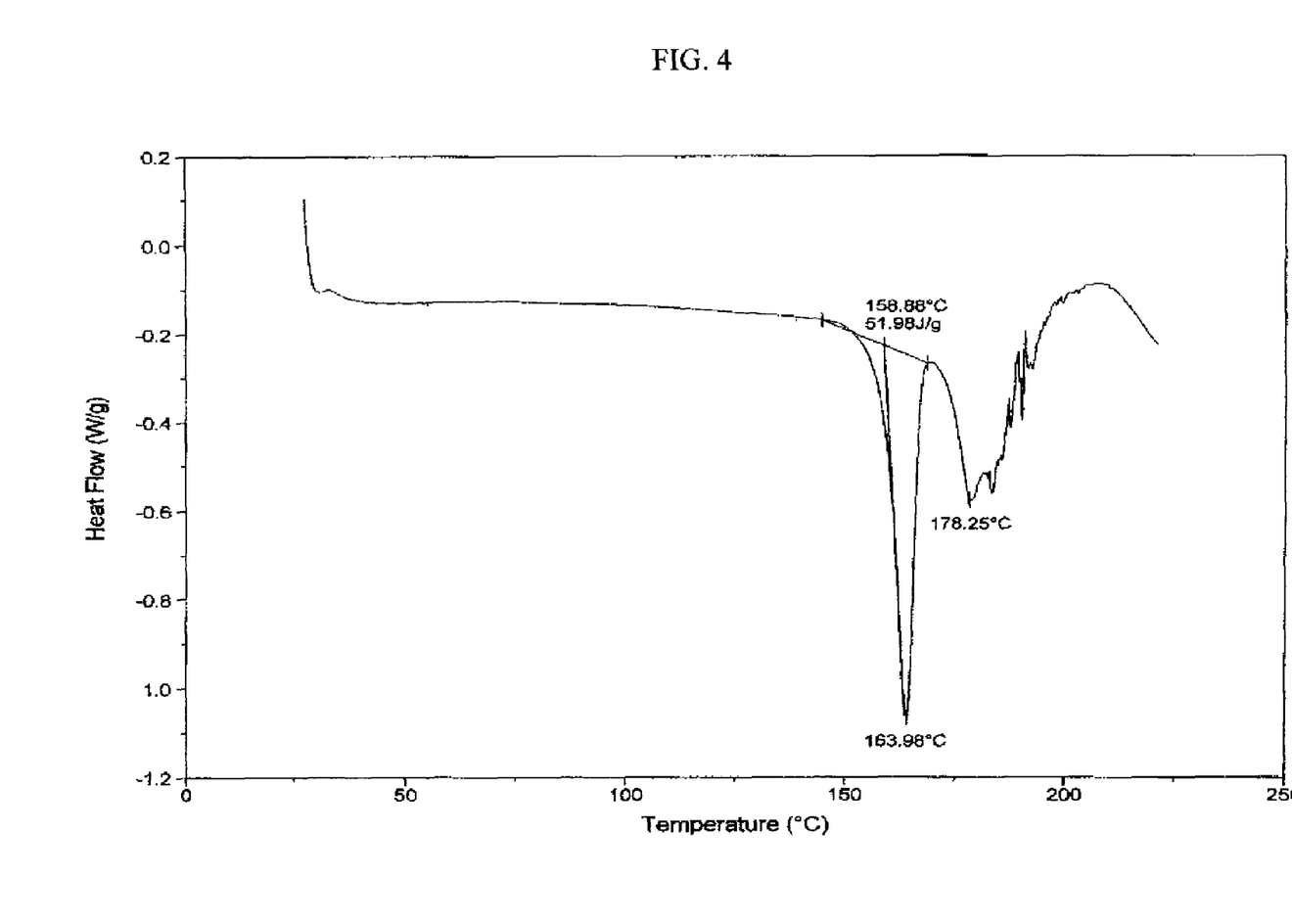
FIG. 4 is the differential scanning calorimetry (DSC) thermogram of crystalline rapamycin 42-ester with 3-hydroxy-2-(hydroxymethyl)-2-methylpropionic acid.

(i) Crystalline rapamycin 42-ester with 3-hydroxy-2-(hydroxymethyl)-2-methylpropionic acid The DSC thermogram of crystalline rapamycin 42-ester with 3-hydroxy-2-(hydroxymethyl)-2-methylpropionic acid is characterized by a sharp melting endotherm at 163.98° C., which endotherm indicates the crystalline nature of rapamycin 42-ester with 3-hydroxy-2-(hydroxymethyl)-2-methylpropionic acid (FIG. 4). The DSC thermogram also includes a degradation product endotherm at 178.25° C.

Figure 5:
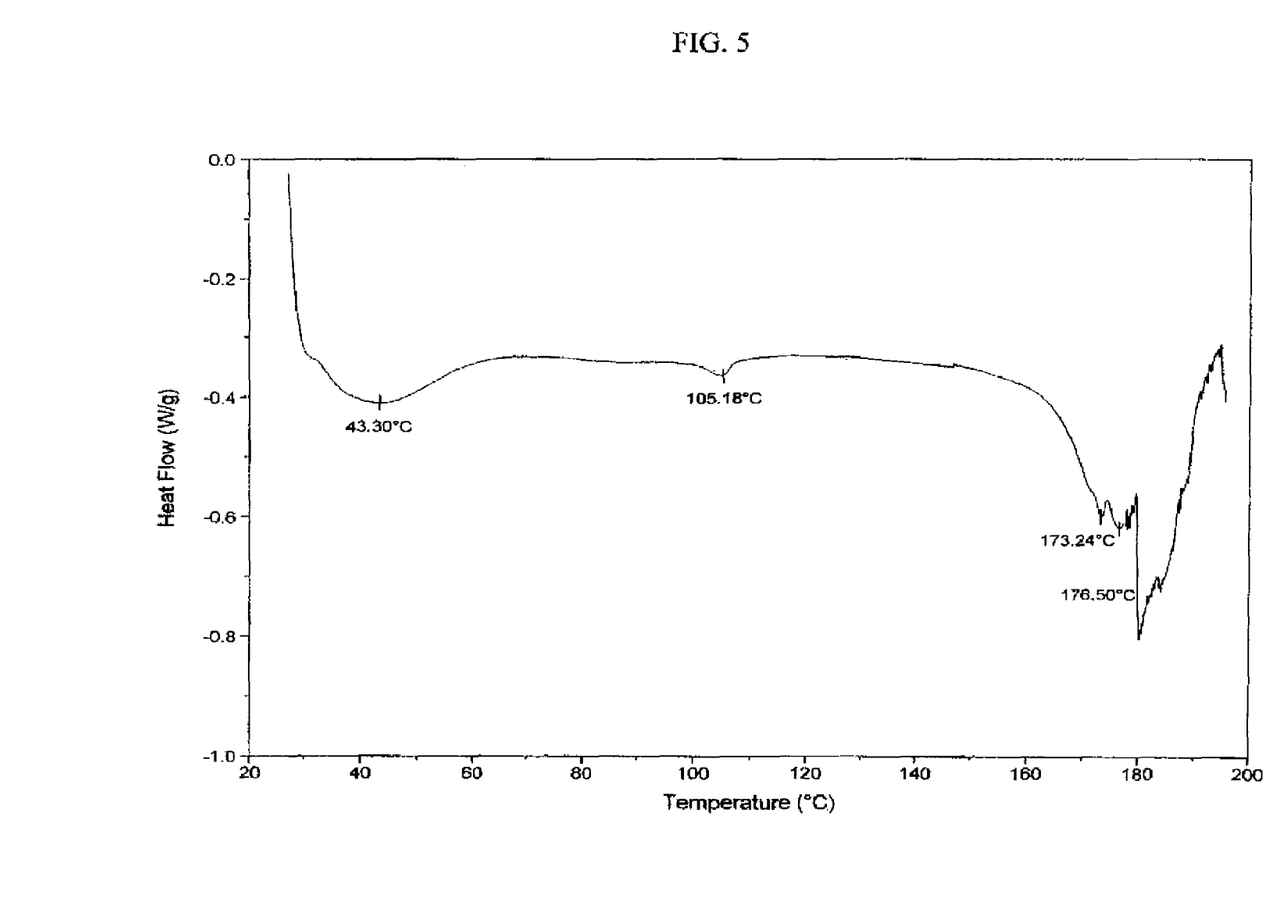
FIG. 5 is the DSC thermogram of amorphous rapamycin 42-ester with 3-hydroxy-2-(hydroxymethyl)-2-methylpropionic acid prepared by evaporation.

(ii) Amorphous rapamycin 42-ester with 3-hydroxy-2-(hydroxymethyl)-2-methylpropionic acid Prepared by Evaporation The DSC thermogram of amorphous rapamycin 42-ester with 3-hydroxy-2-(hydroxymethyl)-2-methylpropionic acid prepared by ethanol evaporation method (batch B1) showed a broad endotherm at 43.30° C. Without wishing to be bound by theory, the inventors have hypothesized that this broad endotherm at 43.30° C. was likely due to residual ethanol and water (FIG. 5). The DSC thermogram also showed a small endotherm at 105.18° C. Possible degradation product endotherms in the DSC thermogram at 173.24° C. and 176.50° C. were also observed.

The characteristic melting endotherm at 163.98° C. for the crystalline form was not present in the DSC thermogram for amorphous rapamycin 42-ester with 3-hydroxy-2-(hydroxymethyl)-2-methylpropionic acid, thereby indicating the presence of the amorphous rapamycin 42-ester with 3-hydroxy-2-(hydroxymethyl)-2-methylpropionic acid.

(iii) Amorphous rapamycin 42-ester with 3-hydroxy-2-(hydroxymethyl)-2-methylpropionic acid Prepared by Precipitation The DSC thermogram of amorphous rapamycin 42-ester with 3-hydroxy-2-(hydroxymethyl)-2-methylpropionic acid prepared by precipitation (batch C1) showed a broad endotherm at about 43.30° C., which was likely due to residual ethanol and water (FIG. 6) as noted above. The DSC thermogram also showed a small endotherm at 105.18° C. Possible degradation product endotherms in the DSC thermogram at 173.24° C. and 176.50° C. were also observed.

Figure 6:
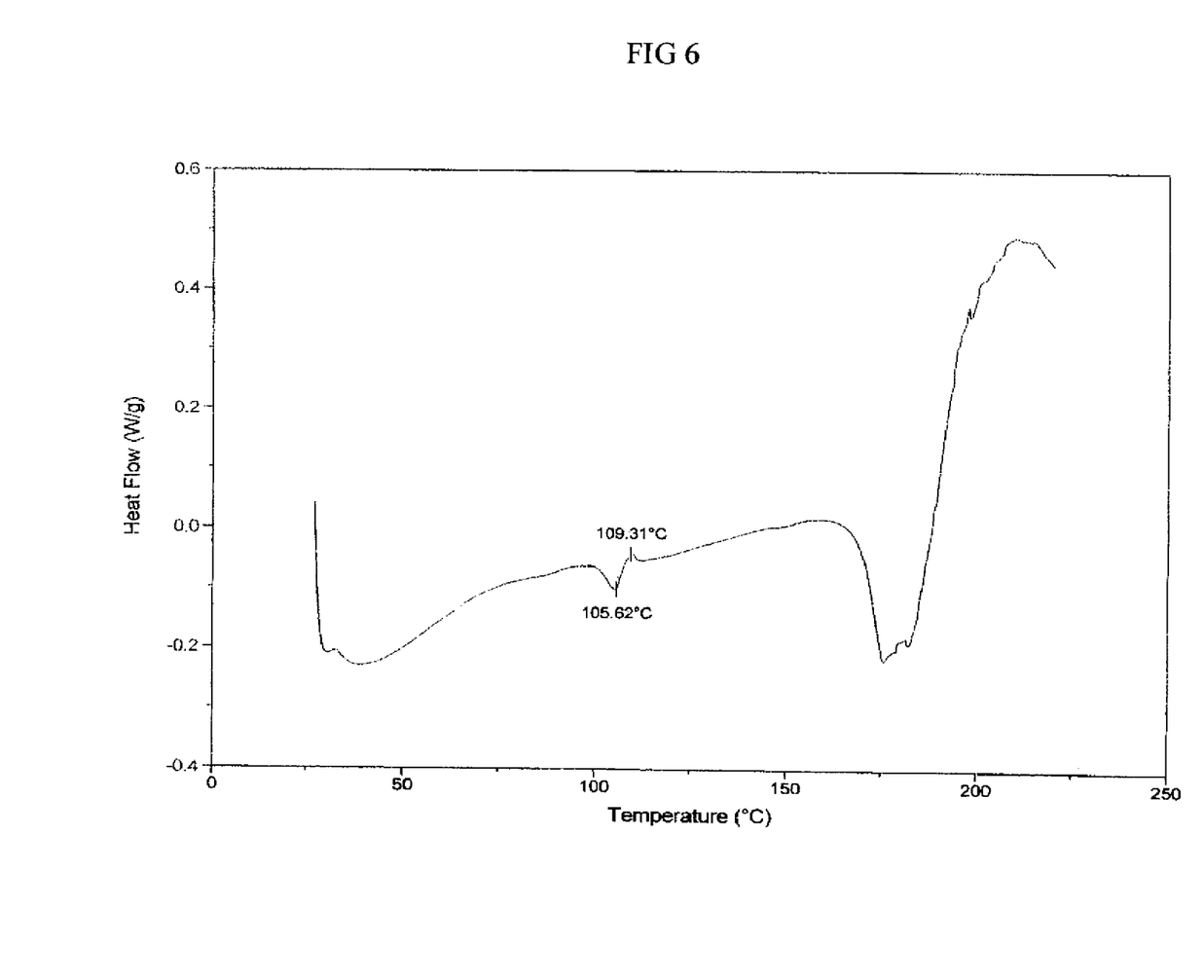
FIG. 6 is the DSC thermogram of amorphous rapamycin 42-ester with 3-hydroxy-2-(hydroxymethyl)-2-methylpropionic acid prepared by precipitation.

The characteristic melting endotherm at 163.98° C. for the crystalline form was not present in this DSC thermogram, thereby indicating the presence of amorphous rapamycin 42-ester with 3-hydroxy-2-(hydroxymethyl)-2-methylpropionic acid.

Figure 7:
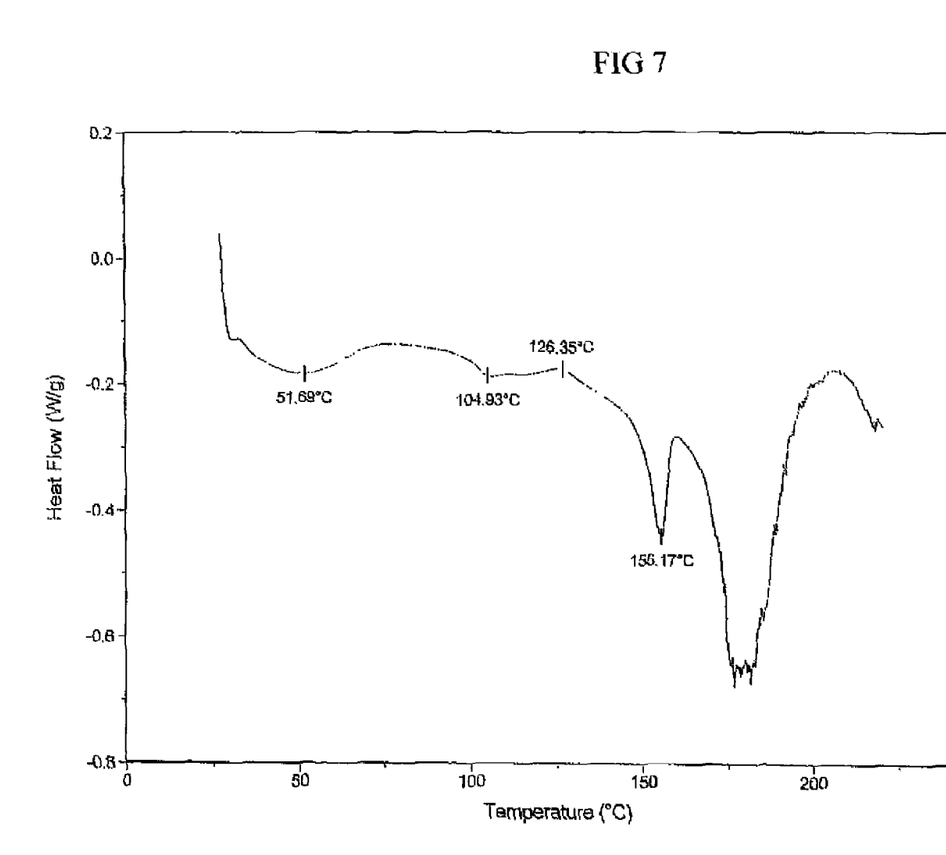
FIG. 7 is the DSC thermogram of amorphous rapamycin 42-ester with 3-hydroxy-2-(hydroxymethyl)-2-methylpropionic acid prepared by ball mill grinding for 60 minutes.

(iv) Amorphous rapamycin 42-ester with 3-hydroxy-2-(hydroxymethyl)-2-methylpropionic acid Prepared by Grinding The DSC thermogram of amorphous rapamycin 42-ester with 3-hydroxy-2-(hydroxymethyl)-2-methylpropionic acid prepared by grinding for 60 minutes (batch D3) showed a decreased intensity and shift of the crystalline endotherm of 163.98° C. to 155.17° C. This shift thereby indicated a substantial decrease in crystallinity of the sample (FIG. 7).

Example 5

Solubility of Amorphous Rapamycin 42-Ester with 3-Hydroxy-2-(Hydroxymethyl)-2-Methylpropionic Acid A. Solubility in Buffer The solubility of amorphous rapamycin 42-ester with 3-hydroxy-2-(hydroxymethyl)-2-methylpropionic acid (batch C4) and micronized crystalline rapamycin 42-ester with 3-hydroxy-2-(hydroxymethyl)-2-methylpropionic acid in a citric acid solution was determined.

Separate samples containing amorphous rapamycin 42-ester with 3-hydroxy-2-(hydroxymethyl)-2-methylpropionic acid (batch C3) (9.1 mg) and micronized crystalline rapamycin 42-ester with 3-hydroxy-2-(hydroxymethyl)-2-methylpropionic acid (41.0 mg) were added to scintillation vials containing 10 g of (0.005 M) citric acid solution containing 0.001% EDTA. The solutions were mixed and maintained at room temperature and a pH of about 4.6. The vials were then shaken on a rotary shaker for 24 hours.

Samples (2 mL) of both of the amorphous and crystalline solutions were withdrawn at selected time intervals (0, 0.5, 3, 5, and 24 h), filtered through a 0.2 μm filter and analyzed at room temperature using high performance liquid chromatography (HPLC) (Table 1). The solubility of the samples was calculated using the data provided in the HPLC chromatograph and techniques used by those skilled in the art and is provided in Table 3.

The solubility of amorphous rapamycin 42-ester with 3-hydroxy-2-(hydroxymethyl)-2-methylpropionic acid was calculated over a period of 24 hours and found to be about 1.88 μg/mL at 25° C., which is 3 times higher than that for the crystalline rapamycin 42-ester with 3-hydroxy-2-(hydroxymethyl)-2-methylpropionic acid. In view thereof, dissolution of amorphous rapamycin 42-ester with 3-hydroxy-2-(hydroxymethyl)-2-methylpropionic acid is thereby faster than the micronized crystalline form.

TABLE 3

| | Solubility (μg/mL) | |
|---|---|---|
| Time (Hours) | Amorphous Batch C3 | Crystalline |
| 0 | 0 | 0 |
| 0.5 | 0.66 | 0.26 |
| 3 | 0.77 | 0.29 |
| 5 | 0.79 | 0.23 |
| 24 | 1.88 | 0.61 |

B. Solubility in Surfactant Solution

The solubility of amorphous rapamycin 42-ester with 3-hydroxy-2-(hydroxymethyl)-2-methylpropionic acid (batch C4) and micronized crystalline rapamycin 42-ester with 3-hydroxy-2-(hydroxymethyl)-2-methylpropionic acid in a surfactant solution was determined.

A 0.005 M citric acid solution containing 0.2% sodium lauryl sulfate and 0.001% calcium EDTA was adjusted to a pH of about 4.73.

Separate samples containing the amorphous rapamycin 42-ester with 3-hydroxy-2-(hydroxymethyl)-2-methylpropionic acid (batch C4) (60 mg) and micronized crystalline rapamycin 42-ester with 3-hydroxy-2-(hydroxymethyl)-2-methylpropionic acid (60 mg) were added to scintillation vials containing 10 g of the citric acid/SLS solution. The solutions were then mixed, maintained at room temperature, and shaken on a rotary shaker for about 24 to about 48 hours.

Samples (2 mL) of both the amorphous and crystalline solutions were withdrawn at 24 h and 48 h, filtered through a 0.2 μm filter and analyzed at room temperature using high performance liquid chromatography (HPLC) (Table 4). Solubilities of the samples were then calculated using the data provided in the HPLC chromatograph and techniques used by those of skilled in the art and is provided in Table 4.

TABLE 4

| Product | Solubility (mg/mL) | |
| --- | --- | --- |
|  | 24 hrs | 48 hrs |
| Amorphous (batch C4) | 2.17 | 2.24 |
| Micronized Crystalline | 0.64 | 0.64 |

The solubility of the amorphous rapamycin 42-ester with 3-hydroxy-2-(hydroxymethyl)-2-methylpropionic acid in the SLS surfactant solution over a period of 24 hours was calculated to be about 2.17 mg/mL at 25° C., which is about 3.5 times higher than that for crystalline rapamycin 42-ester with 3-hydroxy-2-(hydroxymethyl)-2-methylpropionic acid.

In view thereof, dissolution of amorphous rapamycin 42-ester with 3-hydroxy-2-(hydroxymethyl)-2-methylpropionic acid in surfactant solution is also faster than the micronized crystalline form.

Example 6

Stability of Amorphous Rapamycin 42-Ester with 3-Hydroxy-2-(Hydroxymethyl)-2-Methylpropionic Acid The stability of amorphous rapamycin 42-ester with 3-hydroxy-2-(hydroxymethyl)-2-methylpropionic acid was determined at various temperatures over specified periods of time.

Approximately 200 mg of samples of amorphous rapamycin 42-ester with 3-hydroxy-2-(hydroxymethyl)-2-methylpropionic acid prepared by evaporation (batch A1) or precipitation (batch C4) were added to HPLC glass vials, the vials covered with the KIMWIPES® paper (Fisher Scientific) and the KIMWIPES® paper tied to the neck of the vials using wire.

Amorphous rapamycin 42-ester with 3-hydroxy-2-(hydroxymethyl)-2-methylpropionic acid samples prepared by evaporation and the amorphous rapamycin 42-ester with 3-hydroxy-2-(hydroxymethyl)-2-methylpropionic acid prepared by precipitation were then placed in larger glass scintillation vials containing about 1 g of anhydrous calcium sulfate desiccant. The outer scintillation vials were capped, sealed with parafilm and placed in stability chambers. One stability chamber was maintained at a temperature of about 5° C. at about 10-20% relative humidity (RH) and the other stability chamber was maintained at a temperature of about 40° C. at about 75% RH.

The amorphous rapamycin 42-ester with 3-hydroxy-2-(hydroxymethyl)-2-methylpropionic acid samples prepared precipitation were then placed in 4 mL high density polyethylene (HDPE) bottles containing about 2 g of anhydrous calcium sulfate desiccant. The HDPE bottles were sealed using heat induction seals and closed using plastic caps. One bottle was placed in a stability chamber at about 5° C., one bottle was placed in a stability chamber at about room temperature, and the third bottle was placed in a stability chamber at about 40° C. at a RH of about 75%.

Samples of amorphous rapamycin 42-ester with 3-hydroxy-2-(hydroxymethyl)-2-methylpropionic acid samples prepared by evaporation were withdrawn at 1 and 2 weeks (Table 5). Samples of amorphous rapamycin 42-ester with 3-hydroxy-2-(hydroxymethyl)-2-methylpropionic acid samples prepared by precipitation were withdrawn at 1 week and analyzed (Table 6).

TABLE 5

| | Strength = 98.33%, Total Imp. = 0.46%, SLI = 0.19% | | | | | |
| --- | --- | --- | --- | --- | --- | --- |
| | 5° C. | | | 40° C./75% RH | | |
| Initial | Strength (%) | Total Imp (%) | SLI* (%) | Strength (%) | Total Imp (%) | SLI* (%) |
| 1 week | 95.20 | 5.07 | 3.91 | 94.16 | 5.15 | 3.93 |
| 2 weeks | 92.56 | 4.42 | 3.74 | 90.55 | 4.60 | 3.72 |

TABLE 6

| Condition | Time | Strength (%) | Total Imp (%) | SLI (%) | SECO (%) |
| --- | --- | --- | --- | --- | --- |
|  | Initial | 97.93 | 0.41 | 0.20 | ND |
| RT | 1 Week | 97.49 | 0.37 | 0.12 | ND |
| 5° C. | 1 Week | 98.71 | 0.44 | 0.15 | ND |
| 40° C./75% RH | 1 Week | 91.36 | 0.70 | 0.32 | 0.04 |

These data illustrate that samples of amorphous rapamycin 42-ester with 3-hydroxy-2-(hydroxymethyl)-2-methylpropionic acid prepared by precipitation and evaporation are stable.

Example 7

Preparation of tablets Containing Amorphous Rapamycin 42-Ester with 3-Hydroxy-2-(Hydroxymethyl)-2-Methylpropionic Acid Edetic acid (0.008 g), anhydrous citric acid (0.021 g) and a blend of amorphous rapamycin 42-ester with 3-hydroxy-2-(hydroxymethyl)-2-methylpropionic acid prepared by precipitation (batch A1) were mixed geometrically on a paper to form a pre-blend mixture. SLS (2.841 g), anhydrous lactose (17.356 g), povidone (16.521 g) and about 75% of a mixture containing microcrystalline cellulose (MCC) PH 112, NF (35.049 g) and croscarmellose sodium (3.165 g) were passed through a #20 mesh screen. This screened mixture was then combined with the pre-blend mixture containing amorphous rapamycin 42-ester with 3-hydroxy-2-(hydroxymethyl)-2-methylpropionic acid and transferred to a V-blender. The remaining 25% of the MCC and croscarmellose sodium mixture was added to the V-blender and blended for 5 minutes. Magnesium stearate (0.397 g) was added to the blended mixture and blended for an additional 2 minutes.

The final mixture was compressed into 625 mg tablets (Hardness 14-17 kilopond (kp)) using the 0.25×0.71" caplet shaped tooling on a B2 STOKES® Tablet Machine.

The HPLC of each sample was obtained as noted above using a temperature of about 45° C., a flow rate of about 1.0 mL/minute, a detection wavelength of about 280 nm, a 150 mm×4.6 mm YMC PACK® ODS-AM reverse phase column containing 3μ ODS particles, a first mobile phase of an ammonium acetate solution at a pH of about 3.8, acetonitrile, and dioxane at a molar ratio of about 80:52:68, and second mobile phase of an ammonium acetate solution at a pH of about 3.8, acetonitrile, and dioxane at a molar ratio of about 20:34:46. A peak at a retention time of about 21 minutes was observed.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A micronized amorphous form of rapamycin 42-ester with 3-hydroxy-2-(hydroxymethyl)-2-methylpropionic acid,
    said amorphous form having an X-ray diffraction peak pattern comprising abroad halo at 2θ of about 17° and
    a differential scanning calorimetry thermogram lacking the endotherm peak of about 164° for crystalline rapamycin 42-ester with 3-hydroxy-2-(hydroxymethyl)-2-methylpropionic acid.

2. The micronized form according to claim 1, which is prepared by micronizing amorphous rapamycin 42-ester with 3-hydroxy-2-(hydroxymethyl)-2-methylpropionic acid in a jet mill.

3. The micronized amorphous form according to claim 2, wherein said jet mill is a TROST™ mill, an MC JETMILL®, or an ALPINE™ AS spiral jet mill.

4. A solid pharmaceutical composition comprising the micronized amorphous form according to claim 1.

5. A method of preparing a pharmaceutical composition comprising an amorphous form of rapamycin 42-ester with 3-hydroxy-2-(hydroxymethyl)-2-methylpropionic acid, comprising combining the components:
    (i) an amorphous form of rapamycin 42-ester with 3-hydroxy-2-(hydroxymethyl)-2-methylpropionic acid,
    (ii) a metal chelator,
    (iii) a pH adjuster,
    (iv) a surfactant,
    (v) at least one filler,
    (vi) a binder,
    (vii) a disintegrant, and
    (viii) a lubricant.

6. The method according to claim 5, wherein said metal chelator is edetic acid, malic acid, or fumaric acid.

7. The method according to claim 6, wherein said metal chelator is edetic acid.

8. The method according to claim 5, wherein said pH adjuster comprises citric acid, ascorbic acid, fumaric acid, or malic acid.

9. The method according to claim 8, wherein said pH adjuster is citric acid.

10. The method according to claim 5, wherein said surfactant comprises a compound comprising a polysorbate, a compound comprising a sorbitan ester, poloxamer, or sodium lauryl sulfate.

11. The method according to claim 5, wherein said surfactant is sodium lauryl sulfate.

12. The method according to claim 5, wherein said filler is anhydrous lactose, microcrystalline cellulose, mannitol, calcium phosphate, pregelatinized starch, or sucrose.

13. The method according to claim 12, wherein said filler comprises anhydrous lactose.

14. The method according to claim 12, wherein said filler comprises microcrystalline cellulose.

15. The method according to claim 5, wherein said binder comprises povidone, hydroxypropylmethylcellulose, carboxymethylcellulose, or gelatin.

16. The method according to claim 15, wherein said binder is povidone.

17. The method according to claim 5, wherein said disintegrant comprises croscarmellose sodium, a starch, sodium starch glycolate, pregelatinized starch or crospovidone.

18. The method according to claim 17, wherein said disintegrant is croscarmellose sodium.

19. The method according to claim 5, wherein said lubricant comprises magnesium stearate, stearic acid, or sodium stearyl furamate.

20. The method according to claim 19, wherein said lubricant comprises magnesium stearate.

21. The method according to claim 5, wherein said components are dry blended and compressed into a form suitable for administration to a mammalian subject.

22. The method according to claim 5, wherein said components are dry granulated and compressed into a form suitable for administration to a mammalian subject.

23. The method according to claim 5, wherein said components are wet granulated and compressed into a form suitable for administration to a mammalian subject.

24. The method according to claim 23, wherein the form is a tablet or caplet.

25. The method according to claim 23, wherein the form is a liquid suspension.

26. A method of preparing a pharmaceutical composition comprising an amorphous form of rapamycin 42-ester with 3-hydroxy-2-(hydroxymethyl)-2-methylpropionic acid, comprising the steps of:
    (a) combining an (i) amorphous form of rapamycin 42-ester with 3-hydroxy-2-(hydroxymethyl)-2-methylpropionic acid (ii) edetic acid, and (iii) citric acid;
    (b) combining sodium lauryl sulfate, a first portion of anhydrous lactose, povidone, and a first portion of croscarmellose sodium;
    (c) combining the product of (b) with the product of (a);
    (d) combining a second portion of anhydrous lactose and a second portion of croscarmellose sodium with the product of (c);
    (e) blending the product of (d); and
    (f) combining the product of (e) with magnesium stearate.

27. The method according to claim 26, wherein the product of step (b) is passed through a screen.

* * * * *